(12) United States Patent
Rangisetty et al.

(10) Patent No.: US 7,683,175 B2
(45) Date of Patent: Mar. 23, 2010

(54) PROCESS OF MAKING OPTICALLY PURE L-PIPECOLIC ACID AND PROCESS OF MAKING ANESTHETICS AND INTERMEDIATES THEREFROM

(75) Inventors: Jagadeesh B. Rangisetty, Lawrenceville, NJ (US); Manik R. Pullagurla, Lawrenceville, NJ (US); Raja J. J. Muthiah, Plainsboro, NJ (US); Christopher N. Jobdevairakkam, Plainsboro, NJ (US)

(73) Assignee: Navinta, LLC, Ewing, NJ (US)

( * ) Notice: Subject to any disclaimer, the term of this patent is extended or adjusted under 35 U.S.C. 154(b) by 78 days.

(21) Appl. No.: 11/351,072

(22) Filed: Feb. 9, 2006

(65) Prior Publication Data

US 2006/0276654 A1 Dec. 7, 2006

Related U.S. Application Data

(60) Provisional application No. 60/687,838, filed on Jun. 6, 2005.

(51) Int. Cl.
C07D 211/60 (2006.01)
(52) U.S. Cl. .................................................. 546/227
(58) Field of Classification Search .................. 546/227
See application file for complete search history.

(56) References Cited

U.S. PATENT DOCUMENTS

| | | | |
|---|---|---|---|
| 2,897,971 A | | 8/1959 | Gewiss |
| 4,695,576 A | * | 9/1987 | af Ekenstam et al. ....... 514/330 |
| 4,870,086 A | | 9/1989 | Sandberg |
| 5,777,124 A | * | 7/1998 | Zavareh et al. .............. 546/225 |

FOREIGN PATENT DOCUMENTS

| | | |
|---|---|---|
| EP | 1433782 A1 * | 9/2002 |
| EP | 1433782 A1 | 6/2004 |
| JP | 06030789 | 2/1994 |
| JP | 2000178253 | 6/2000 |
| WO | WO-8500599 | 2/1985 |
| WO | WO-9601185 | 1/1996 |
| WO | WO-03024930 A1 | 3/2003 |

OTHER PUBLICATIONS

B. Ho et al., "Synthesis of 2-piperidinecarboxylic acid derivatives.", Sep. 25, 1997, Eur. J. Med. Chem 33 (1998) 23-31, Elsevier Paris.
M. Chen et al., "Kinetic Resolution of Pipecolic Acid Using Partially-Purified Lipase from *Aspergillus niger*.", Dec. 14, 1993, J. Org. Chem. 1994, 59, 2075-2081, Montreal, CA.
H. Federsel et al., "An Efficient Synthesis of a New, Chiral 2', 6' —Pipec. . . . ", 1987, Acta Chem. Scand., Ser. B41: 751-761, Sodertalje, Sweden.
Kim et al., "Optical Resolution of DL-Pipecolic Acid by Fermentation Uisng Pseudomonas. . . . " J. Microbiol. Biotechnol (2001), 11(2), 217-221, Seoul, South Korea.
D. Kozma et al. ,"Control Temperature when Doing Resolutions", Optical Resolutions, Nov. 2003, UK.
T. Fujii et al., "Biotransformation of L-Lysine to L-Pipecolic Acid . . . ", Biosci. Biotechnol. Biochem., 66(3), 622-627, 2002, Fujisawa, Japan.

* cited by examiner

*Primary Examiner*—D. Margaret Seaman
*Assistant Examiner*—Nizal S Chandrakumar
(74) *Attorney, Agent, or Firm*—William J. Sapone; Coleman Sudol Sapone P.C.

(57) ABSTRACT

The present invention describes a novel process of preparation of optically pure L-Pipecolic acid and an improved process for the conversion of L-pipecolic acid to L-N-(2,6-dimethylphenyl)-1-propyl-2-piperidinocarboxamide, its hydrochloride salt and hydrochloride monohydrate.

3 Claims, 2 Drawing Sheets

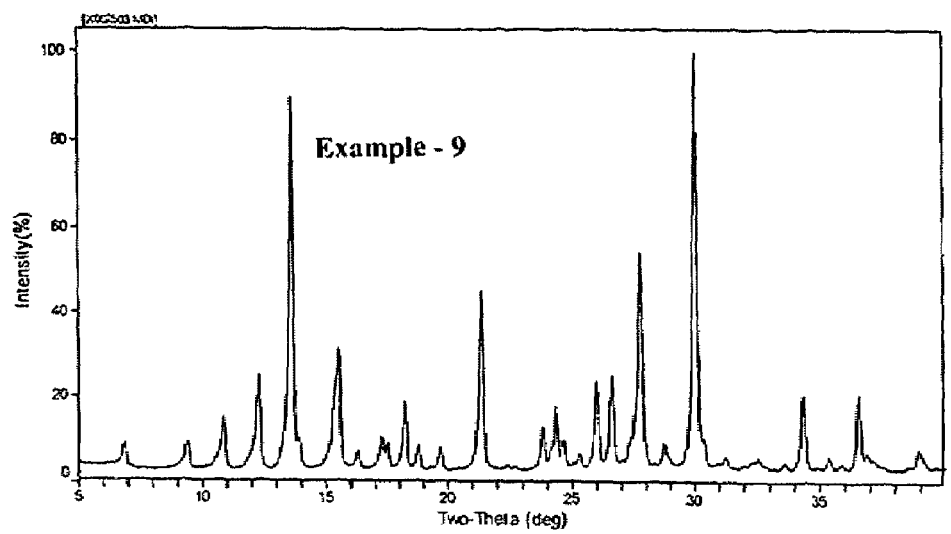
Figure-1 X-Ray powder diffraction pattern of L-Ropivacaine hydrochloride monohydrate
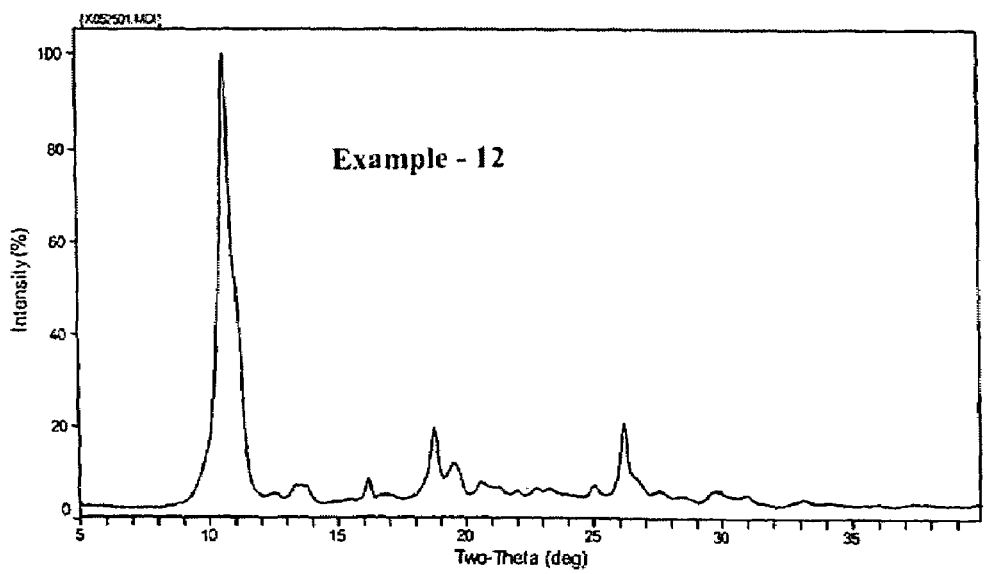
Figure-2 X-Ray powder diffraction pattern of L-Ropivacaine hydrochloride

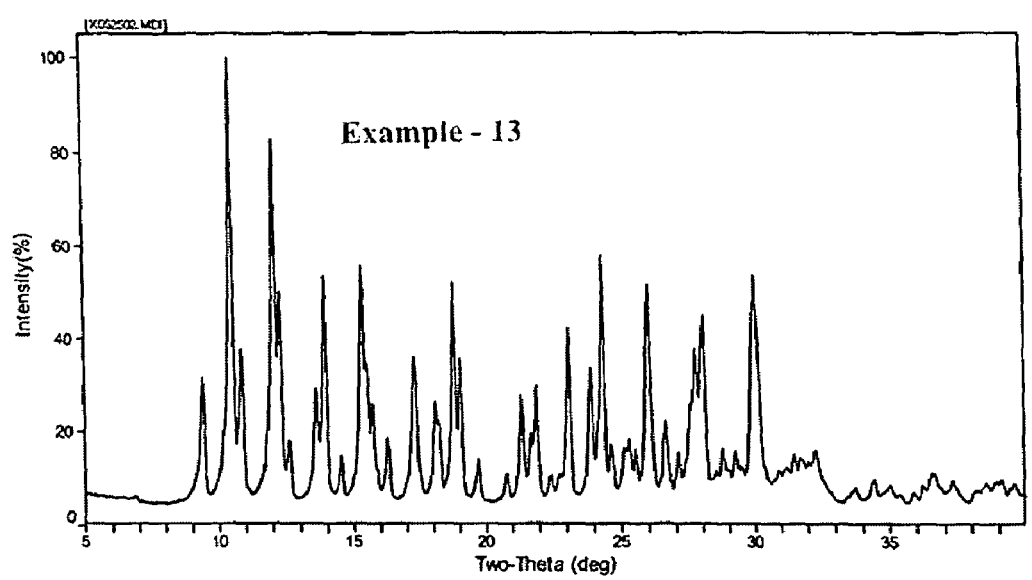
Figure-3 X-Ray powder diffraction pattern of Hydrated L-Ropivacaine hydrochloride

PROCESS OF MAKING OPTICALLY PURE L-PIPECOLIC ACID AND PROCESS OF MAKING ANESTHETICS AND INTERMEDIATES THEREFROM

RELATED APPLICATIONS

This application is based on provisional application 60/687,838, filed 6 Jun. 2005, the disclosure of which is incorporated herein by reference.

BACKGROUND OF THE INVENTION

1. Field of the invention

The present invention relates to the preparation of enantiomerically and chemically pure L-pipecolic acid by using optically active resolving agents. The present invention also relates to preparing enantiomerically pure L-N-(2,6-dimethylphenyl)-1-propyl-2-piperidinocarboxamide, its hydrochloride salt, and the hydrochloride monohydrate from L-pipecolic acid.

2. The State of the Art

L-pipecolic acid, also known as piperidino-2-carboxylic acid, is an amino acid, more specifically a cyclic imino acid, that can be isolated from a variety of natural sources. Optically active L-pipecolic acid is used as an intermediate in the synthesis of the local anesthetics, such as levo-bupivacaine and ropivacaine. Ropivacaine is the generic name of the n-propyl homolog of the recently introduced long active local anesthetics having the general formula N-(n-alkyl)-2,6-dimethylpheny-piperidine-2-carboxamide. Optically pure ropivacaine is the levo form of N-(n-propyl)-2,6-dimethylphenyl-piperidine-2-carboxamide. Another chemical name for ropivacaine is (L) N-n-propylpipecolic acid-2,6-xylidide. The optically pure form of ropivacaine is reported to have reduced cardio-toxic potential compared to the racemic mixture of bupivacaine (racemic N-n-butylpipecolic acid-2,6-xylidide, having better analgesic effects than either D or L isomer alone, as described in U.S. Pat. No. 4,695,576)

Based on the biological results of testing (L)-enantiomer of ropivacaine as described in U.S. Pat. No. 4,695,576, it has been reported that L-enantiomers display lower cardiotoxicity than the corresponding racemates whilst maintaining the same anesthetic potency, and are therefore potentially more beneficial for clinical use. Thus it is advantageous to have an efficient and safe process for producing L-ropivacaine and its salts in the form of single enantiomer.

Preparation of optically pure L-pipecolic acid by different methods has been described in the art. Most typically, the art uses an optically pure resolving agent, most commonly optically pure tartaric acid, although enzymatic methods have also been disclosed.

WO 85/00599 and U.S. Pat. No. 4,695,576 each describes a method of preparing L-N-n-propylpipecolic acid-2,6-xylidide by condensing L-pipecolic acid chloride hydrochloride with 2,6-xylidine using L-pipecolic acid having a purity of about 90% (that is, about 90% in the levo form, 90% optical purity). It is disclosed in these patents that the 90% pure L-pipecolic acid was obtained by resolving DL-pipecolic acid with L-tartaric acid alone.

Eur. J. Med. Chem. 33 (1998) 23-31 has described the preparation of L-pipecolic acid by resolving DL-pipecolic acid with only D-(−)-tartaric acid and Amberlite resin. The conditions described for the resolution are seen to be inefficient, presenting low yields. Further, the use of D-tartaric acid alone would be expensive and thus such a process is economically unfeasible.

WO 961185 describes a process for the preparation of optically enriched pipecolic acid as a salt with an optically active acid. Exemplified in this publication is the use of DL-pipecolic acid, D-tartaric acid and butyric acid heated to 110° C. for four hours to form (L)-pipecolic acid-D-tartrate salt which is then converted to (L)-pipecolic acid.

Acta. Chem. Scand. B41: 757-761, 1987 describes use of iso-propanol in combination with various water contents for the resolution step. These combinations gave varying yields and quality. It has been suggested that optical resolution of pipecolic acid xylidines with iso-propanol or ethanol has an increasing yield but a decreasing optical purity as the temperature of the resolution is decreased. "Optical resolutions, theory and practice," Kozma and Marthi, Scientific Update Training Course (Mayfield, UK), November 2003.

JP 2000178253 describes a method for preparation of optically active pipecolic acid by resolving with optically active 2-phenoxy propionic acid.

Resolution has also been accomplished enzymatically. J. Microb. Biotech. 11 (2) (2001) 217-221 describes a method for optical resolution of DL-pipecolic acid by fermentation using *pseudomonas* sp. PA09. J. Org. Chem. 59 (8) (1994) 2075-2081 describes a process for the resolution of pipecolic acid using partially purified lipase from *Aspergillus niger*, yielding 93% enantiomeric excess of (S)-pipecolic acid and this compound needs further purification. J. Biosci. Biotech. Biochem 66 (2002) 622 describes a process for enzymatic conversion of L-lysine to L-pipecolic acid with an enantiomeric purity of 100%. JP 06030789 describes a process for preparing L-pipecolic acid by treating DL-pipecolic acid with D-amino acid oxidase and sodium borohydride.

Unfortunately, none of the foregoing resolution procedures establishes a practical and economic method for obtaining pure L-pipecolic acid having an enantiomeric purity greater than 99%. The conventional resolution processes described in prior art afford up to 90% of the L-isomer of pipecolic acid. Thus a process for preparing pure L-pipecolic acid is very much in need for the economic and safe production of pure pharmacologically active L-Ropivacaine, and its salts (and hydrates thereof).

Some of the disadvantages of these resolution processes described in the prior art are:

(1) Optical resolution of DL-pipecolic acid by the use of either L or D optically active resolving agents results in enantiomeric purity of only about 90% and the product contains D-pipecolic acid as an impurity (U.S. Pat. No. 4,870,086). L-Ropivacaine prepared from 90% optically pure L-pipecolic acid thus requires additional purification at some intermediate stage or at the final stage, thereby leading to lot of yield loss and manufacturing difficulties. The procedure for preparing L-pipecolic acid chloride hydrochloride using phosphorous pentachloride at a temperature of about 35° C. and then further conversion to xylidide at temperature of about 70° C. gives an even lower yield.

(2) L-pipecolic acid prepared by enzymatic conversion of L-Lysine or enzymatic resolution of DL-pipecolic acid method results in 100% enantiomeric purity. However, such methods are expensive and require more controls (and capital investment) for monitoring the reaction.

(3) It has been reported that the L-N-n-propylpipecolicacid-2,6-xylidide hydrochloride described in WO 85/00599 and U.S. Pat. No. 4,695,576 contains 10% of the D-(+) enantiomer of N-n-propylpipecolic acid-2,6-xylidide hydrochloride as an impurity. In addition, the product is hygroscopic, contains 2% water, and is physically unstable.

Most of the synthetic processes reported in the art for preparing Ropivacaine involve the use of a chlorinating agent to condense the L-pipecolic acid with xylidine.

U.S. Pat. No. 4,695,576 describes the use of phosphorus pentachloride in acetyl chloride at a temperature of 35° C. to convert L-pipecolic acid hydrochloride to L-pipecolic acid chloride hydrochloride. The L-pipecolic acid chloride hydrochloride is further condensed with 2,6-xylidine in a mixture of acetone and N-methylpyrrolidone to give L-N-pipecolyxylidide.

U.S. Pat. No. 5,777,124 describes a process for preparing levo-bupivacaine and its analogues by the one pot conversion of L-pipecolic acid to L-N-pipecolyxylidide using hydrochloric acid and thionyl chloride at a temperature of 55° C.

EP 1433782 describes a process for producing pipecolamide derivatives by reacting pipecolic acid and xylidine in presence of a condensation agent such as dicyclohexycarbodiimide, methane sulfonyl chloride, phosphoryl chloride. The reactions were performed at a temperature of 50° C. to room temperature.

The major disadvantages with these synthetic processes are:
(1) The handling of phosphorous pentachloride is problematic on a manufacturing scale at temperatures around 35° C., as in the '576 patent, because of the liberation of acid fumes.
(2) The reaction of L-pipecolic acid chloride hydrochloride with 2,6-xylidine at 70° C. poses problems with the instability of L-pipecolic acid chloride hydrochloride, the yield of L-N-pipecolyxylidide is low, and it is difficult to isolate the product from the reaction medium.
(3) The reaction of L-pipecolic acid chloride hydrochloride with 2,6-xylidine in a mixture of acetone and N-methylpyrrolidone, as advocated in the art, again yields a product that is difficult to isolate from the reaction medium.
(4) The handling of thionyl chloride at a higher temperature suitable for its use at an industrial scale is difficult, requiring special personnel, and the reaction generates harmful gases (posing environmental and safety problems).

BRIEF DESCRIPTION OF THE FIGURES

FIG. 1 is an x-ray diffraction pattern of the L-ropivacaine hydrochloride monohydrate obtained in Example 9.

FIG. 2 is an x-ray diffraction pattern of the L-ropivacaine hydrochloride obtained in Example 12.

FIG. 3 is an x-ray diffraction pattern of the hydrated L-ropivacaine hydrochloride obtained in Example 13.

SUMMARY OF THE INVENTION

In light of the foregoing deficiencies in the art, one object of this invention is to provide a process for preparing optically pure L-pipecolic acid by an efficient and safe method.

Another object of the present invention is to provide an efficient method for preparing L-N-pipecolyxylidide in the absence of N-methylpyrrolidone. Another object of this invention is to provide such method with improved results in comparison with the art. The compound is useful in the preparation of the above-noted anesthetics.

Yet another object of this invention is to provide processes for preparing N-n-propylpipecolicacid-2,6-xylidide, its hydrochloride salt, and it hydrated hydrochloride salt with better yields as compared with the art.

A further object of the present invention is to provide a process for preparing enantiomerically pure L-N-(2,6-dimethylphenyl)-1-propyl-2-piperidinocarboxamide, its hydrochloride salt and hydrochloride monohydrate, and especially where such production is from enantiomerically and chemically pure L-pipecolic acid.

Yet a further object of this invention is to provide a method for converting L-N-(2,6-dimethylphenyl)-1-propyl-2-piperidinocarboxamide to its hydrochloride monohydrate in single step.

In one embodiment this invention provides method for preparing optically pure L-pipecolic acid by resolving DL-pipecolic acid first with D- or L-tartaric acid and then purifying by resolution with L- or D-tartaric acid, respectively. In a specific embodiment, the L-pipecolic acid enantiomer is separated from a racemic DL-pipecolic acid with the use of L-tartaric acid to remove the unwanted isomer and the desired enantiomer is then further purified with D-tartaric acid to obtain L-pipecolic acid with a desirable and commercially useful optical purity.

In another embodiment this invention utilizes enantiomerically pure L-pipecolic acid to produce an optically pure (>99.5% purity) N-(n-alkyl)-2,6-dimethylpheny-piperidine-2-carboxamide, such as L-N-(2,6-dimethylphenyl)-1-propyl-2-piperidinocarboxamide (i.e., ropivacaine). The optical purity of N-n-propylpipecolic acid-2,6-xylidide prepared from such pure L-pipecolic acid is greater than 99% and it can be purified further.

In yet another embodiment, the optically pure free base of ropivacaine is utilized for the preparation of ropivacaine hydrochloride and hydrochloride monohydrate, based on the surprising discovery that L-N-(2,6-dimethylphenyl)-1-propyl-2-piperidinocarboxamide free base can be converted in single step to L-N-(2,6-dimethylphenyl)-1-propyl-2-piperidinocarboxamide hydrochloride monohydrate.

DETAILED DESCRIPTION OF THE SPECIFIC EMBODIMENTS

As explained above, optically pure L-pipecolic acid is a compound commercially useful for the preparation of various anesthetics, especially optically pure anesthetics, having the general formula N-(n-alkyl)-2,6-dimethylpheny-piperidine-2-carboxamide, especially L-N-(2,6-dimethylphenyl)-1-propyl-2-piperidinocarboxamide (i.e., ropivacaine), which anesthetics are often provided commercially in the form of a hydrate and/or a hydrochloride. Specific embodiments of this invention describe the preparation of the optically pure starting material, the anesthetic, and the hydrochloride monohydrate, it being understood that various instances of the practice of this invention is illustrated by the following examples should be understood to be exemplary and not limiting.

With regard to a desired starting material for producing anesthetics, a racemic mixture of DL-pipecolic acid is resolved twice to yield the desired L-pipecolic acid. The sequential resolutions used D- or L-tartaric acid and then L- or D-tartaric acid, respectively, to yield the desired L-pipecolic acid product having an optical purity of at least about 70%, more preferably at least about 98% purity, even more preferably at least about 99% optical purity, and most preferably having an optical purity of at least 99.5%. The resolving agent is present at from about 2% to about 50% on a molar basis with respect to the pipecolic acid to be resolved. Although the examples use optically pure tartaric acid (≧99% purity), which are commercially available, other optically pure resolving agents can also be used, including substituted tartaric acids.

EXAMPLE 1

Preparation of L-pipecolic Acid from DL-pipecolic Acid by Resolving First with L-tartaric Acid Followed by Resolving with D-tartaric Acid.

Resolution: 1

To a mixture of about 3000 mL of 95% ethanol and 200 mL water at about 80° C. was added about 200 g of DL-pipecolic acid followed by 244 g of L-tartaric acid. The reaction mixture was stirred at 80° C. for about an hour to get a clear solution. The solution was then allowed to stand at about 25° C. for about 48 h and the solid precipitated was filtered. The filtrate was reduced to 1300 mL by evaporation and allowed to stand at about 25° C. for about 24 h. More solid precipitated out was removed by filtration The filtrate was evaporated to dryness and the residue was dissolved in 1 L water. (all water used herein is distilled, unless otherwise noted) The aqueous solution was treated with Amberlite Ion-Exchange resin IR-120 H+ form (hydrous form) to remove the tartaric acid, followed by 10% $NH_4OH$ solution treatment of the resin to recover the L-pipecolic acid of an optical purity of about 85-90% of L-isomer. After drying, 110 g of a solid was obtained. (All temperatures and times are approximations within a margin of error that is typical for these types of reactions and processes and should be understood by those of ordinary skill in these arts as such.)

Resolution 2: To a solution of 1400 ml of 95% ethanol and 100 ml water at 80° C. was added 110 g of 85-90% pure of L-pipecolic acid obtained as described above, followed by the addition of 134 g of D-tartaric acid. The aqueous mixture was stirred at about 80° C. for about 1 h, by which time the solution became clear. The solution was allowed to stand at room temperature for about 24 h (1 day) and the solid obtained was filtered to give 150 g pipecolic tartrate salt. The solid obtained was then dissolved in 1 L of water. The water solution was treated with Amberlite Ion-Exchange resin IR-120 H+ form (hydrous form; available from Rohm & Hass Co., Philadelphia, Pa.) to remove tartaric acid, followed by extraction using 10% $NH_4OH$ solution to recover from the resin to L-pipecolic acid having at least 99.5% purity. After drying, 65 g of L-pipecolic acid was obtained. $[\alpha]_D^{25}=-26.0°$

EXAMPLE 2

Preparation of L-pipecolic Acid from DL-pipecolic Acid by Resolving First with D-tartaric Acid Followed by Resolving with L-tartaric Acid Resolution: 1

To a mixture of about 600 mL of 95% ethanol and 200 mL water at 80° C. was added about 40 g of DL-pipecolic acid followed by the addition of 49 g of D-tartaric acid. The reaction mixture was stirred at 80° C. for about an hour to get a clear solution. The solution was allowed to stand at about 25° C. for about 48 hrs and the solid precipitated was filtered. The filtrate was reduced to 260 mL by evaporation and allowed to stand at about 25° C. for 24 h. At the end of that period, more solid had precipitated out and was removed by filtration The filtrate was evaporated to dryness and the residue was dissolved in 1 L water. The water solution recovered was then treated with Amberlite Ion-Exchange resin IR-120 H+ form (Hydrous form) to remove the tartaric acid followed by 10% $NH_4OH$ solution treatment of the resin to give L-pipecolic acid of optical purity of about 85-90%. After drying 22 g of a solid was obtained.

Resolution 2: To a solution of 280 ml of 95% ethanol and 100 ml water at 80° C. was added 22 g of the L-pipecolic acid with optical purity of 85-90% produced by Resolution 1, followed by the addition of 27 g of L-tartaric acid. The reaction was stirred at 80° C. for 1 h by which time the solution became clear. The solution was then allowed to stand at room temperature for 24 h and the solid resulting was filtered to give 10 g pipecolic tartrate. The mother liquor was treated with Amberlite Ion-Exchange resin IR-120 H+ form (hydrous form) to remove tartaric acid, followed by 10% $NH_4OH$ solution treatment to recover from the resin L-pipecolic acid having an optical purity of at least 99.5%. After drying, 12 g of the ≧99.5% optical purity L-pipecolic acid was obtained. $[\alpha]_D^{25}=-26.0°$

EXAMPLE 3

Preparation of L-pipecolic Acid Hydrochloride from the Acid in a Single Step

A solution of 150 g of L-pipecolinic acid (1170 mmol) in methanol (3000 ml) was stirred at room temperature for 10 to 15 min, after which was added 900 mL of saturated methanolic HCl slowly over a period of 20 to 30 min; stirring continued until a clear solution was formed (after about 20 to 30 min). The methanol was then removed by vacuum distillation and the solid obtained was dried to give pure L-pipecolic acid hydrochloride (192.3 g)

L-N-pipecolylxylidide is a useful material for the manufacture of the above-noted anesthetics. As shown by the following three examples, it can be produced using phosphorous pentachloride at an elevated temperature, as in the above-noted art, at relatively lower yields, or at a reduced temperature with significantly higher yields. The use of a reduced temperature allows safer handling of the phosphorous pentachloride with reduced generation of fumes. The process is conducted at −30° to +20° C., more preferably at about −30° C. to 0° C. and most preferably at about −30° C. to −10° C.

EXAMPLE 4

Preparation of L-N-pipecolylxylidide at Elevated Temperature

To a suspension of 19.25 g of L-pipecolinic acid HCl (112 mmol) in acetyl chloride (115 mL) at about 35-40° C. was added 19.25 g of phosphorous pentachloride (92.5 mmol) slowly over a period of 20 to 30 min and stirred over a period of 2 h. Then a second lot of 9.6 g of phosphorous pentachloride (46 mmol) was added to the reaction mixture over a period of 10 to 20 min and stirring continued for another 4.5 h at a temperature of about 35-40° C. The suspension was filtered and the solid washed with cold toluene (100 mL) followed by cold acetone (150 mL) to give L-pipecolic acid chloride hydrochloride (36%): mp 130° C.

The solid L-pipecolic acid chloride hydrochloride just obtained was suspended in acetone (300 ml) and kept at temperature of about 35 to 40° C.; then 2,6-dimethylaniline (28 mL, 250 mmol) was added dropwise. The reaction mixture was stirred for 12 h. The precipitated solid material was isolated by filtration and washed with acetone. The isolated and washed solid was then dissolved in water and adjusted to pH 12 with sodium hydroxide (50%) solution (7 mL). The aqueous layer was extracted with ethyl acetate (3×100 mL) and the combined organic layers were washed with brine (75 mL). The organic layer was dried over $Na_2SO_4$ and evaporated to give L-N-pipecolylxylidide: mp 128-130° C., Yield 45 %

EXAMPLE 5

Preparation of L-N-pipecolylxylidide at Reduced Temperature.

To a suspension of 19.25 g of L-pipecolinic acid HCl (112 mmol) in acetyl chloride (115 mL) at about 0 to −5° C. was added 19.25 g of phosphorous pentachloride (92.5 mmol) slowly over a period of 20 to 30 min and stirred over a period of 2 h. while maintaining the temperature. Then a second lot of 9.6 g of phosphorous pentachloride (46 mmol) was added to the reaction mixture over a period of 10 to 20 min and stirring continued at the same temperature for another 4.5 h. The suspension was then filtered and the solid washed with cold toluene (100 mL) followed by cold acetone (150 mL) to give L-pipecolic acid chloride hydrochloride (62%): mp 130° C.

The solid hydrochloride just obtained was suspended in acetone 300 mL kept at temperature of about 0 to −5° C. and 2,6-dimethylaniline (28 mL, 250 mmol) was added dropwise. The reaction mixture was stirred for 12 h at the same temperature. A precipitated solid material was isolated by filtration and washed with acetone. The washed precipitated solid was dissolved in water and adjusted to pH 12 with sodium hydroxide (50%) solution (7 mL ). The aqueous layer was extracted with ethyl acetate (3×100 mL) and the combined organic layers were washed with brine (75 mL). The organic layer was dried over $Na_2SO_4$ and evaporated to give L-N-pipecolylxylidide: mp 128-130° C., Yield 61%.

EXAMPLE 6

Preparation of L-N-Pipecolylxylidide at Reduced Temperature

To a suspension of 19.25 g of L-pipecolinic acid HCl (112 mmol) in acetyl chloride (115 ml) at about −30 to −20° C. was added 19.25 g of phosphorous pentachloride (92.5 mmol) slowly over a period of 20 to 30 min and stirred while maintaining the temperature over a period of 2 h. Then a second lot of 9.6 g of phosphorous pentachloride (46 mmol) was added to the reaction mixture over a period of 10 to 20 min and stirring continued at the same temperature for another 4.5 h. The suspension was filtered and the solid washed with cold toluene (100 mL) followed by cold acetone (150 mL) to give pipecolic acid chloride hydrochloride (21 g): mp 130° C.

The solid hydrochloride just obtained was suspended in acetone 300 ml and kept at about the same temperature (about −30° C. to about −20° C.) and 2,6-dimethylaniline (28 mL, 250 mmol) was added drop wise. The reaction mixture was stirred for 12 h at this temperature. A precipitated solid material was isolated by filtration and washed with acetone. The solid was dissolved in water and adjusted to pH 12 with sodium hydroxide (50%) solution (7 mL). The aqueous layer was extracted with ethyl acetate (3×100 mL) and the combined organic layers were washed with brine (75 mL). The organic layer was dried over $Na_2SO_4$ and evaporated to give 19 g of L-N-pipecolylxylidide: mp 128-130° C., Yield 71 %

EXAMPLE 7

Preparation of L-ropivacaine Free Base from L-N-pipecolylxylidide

To a solution of L-N-pipecolylxylidide (10 g, 43 mmol) in iso-propanol (40 mL) was added potassium carbonate (4 g), 1-bromopropane (10 mL ), and water, and the mixture was heated at 72° C. for 2 h. An additional amount of 1-bromopropane (2 mL) was added to the reaction mixture at 72° C. and the mixture was stirred until visual disappearance of the starting material. To a mixture of toluene (75 mL) and water (75 mL) heated to 50° C. was added the reaction mixture and the resulting reaction mixture was stirred for 10 min. The organic layer was separated and washed with water (2×50 mL) at 40° C., followed by washing with saturated sodium bicarbonate solution (75 mL) and then washing with brine (75 mL) at room temperature. The toluene layer was dried over $Na_2SO_4$ and evaporated to give a white solid, which was recrystallized from 90 ml ethylacetate to give 10 g of the pure free base. The L-ropivacaine obtained was at least 99.5% chemically and optically pure. mp 142-144° C., Yield 84%.

The hydrochloride monohydrate of ropivacaine can be prepared from L-ropivacaine in a very simple process. The L-ropivacaine is dissolved in acid at a temperature ranging from room temperature (about 25° C.) to an elevated temperature (about 90° C.) while being stirred. The solution is then cooled while stirring is continued, and a solid hydrochloride monohydrate precipitate is recovered.

EXAMPLE 8

Preparation of L-ropivacaine Hydrochloride Monohydrate

About 2 g of Ropivacaine base was dissolved in a mixture of 2.6 mL of concentrated hydrochloride acid and 5 mL of water at about 30° C. This mixture was stirred at a temperature of about 50° C. for about 30 min and then hot acetone (100 mL) was added. The mixture was then held at about 0 to 5° C. and stirring continued for about 2 hr. A precipitated solid was filtered, washed with acetone, and then dried under vacuum at about 35° C. for about 6 hr. 2.1 g, yield 93%, water content: 5.5%. All water contents herein are determined by Karl Fisher titration.

EXAMPLE 9

Preparation of L-Ropivacaine Hydrochloride Monohydrate

About 2 g of Ropivacaine base was dissolved in a mixture of 2.6 mL of concentrated hydrochloride acid and 40 mL of water. The solution was heated to about 85° C. and stirred for about 30 min to get a clear solution and cooled to about 5° C. and continued stirring for about 2 hr. A precipitated solid was recovered and filtered, then washed with acetone and dried under vacuum at about 35° C. for about 6 hr. Results: wt 2.0 g, yield 88.5 %; water content: 5.5%. The x-ray diffraction pattern of the material obtained is shown in FIG. 1.

EXAMPLE 10

Preparation of L-Ropivacaine Hydrochloride Monohydrate

About 2 g of Ropivacaine base was dissolved in 10 mL of water and 7.3 mL of concentrated hydrochloride acid was added slowly with stirring and 350 mL of acetone was added and kept at about 0° C. for 2 days. The precipitated solid was filtered, washed with acetone, and dried under vacuum at about 35° C. for about 6 hr: 1.8 g; yield 79%; water content of 5.6%.

EXAMPLE 11

Preparation of L-Ropivacaine Hydrochloride Monohydrate

About 3 g of Ropivacaine base was dissolved in 10 mL of water and to this solution was added 50 mL of hot acetone and conc. Hydrochloride acid was added slowly with stirring until pH reaches 2 and heated to reflux until the solution becomes clear solution. 20 mL of acetone was added and the precipitated solid was filtered, washed with acetone and dried to give L-Ropivacaine hydrochloride monohydrate 2.9 g, yield 82% Water content: 5.6%

The hydrochloride of L-ropivacaine can be obtained by removing the water from L-ropivacaine hydrochloride monohydrate. The water is removed by gentle heating under vacuum. Gentle heating is preferred to provide the desired product in a reasonable amount of time, although use of a vacuum at room temperature may be sufficient but lengthy.

EXAMPLE 12

Preparation of L-Ropivacaine Hydrochloride

About 5 g of L-Ropivacaine hydrochloride monohydrate solid was heated in an oven to about 85° C. under vacuum for about 6 hr. The temperature of the oven is reduced to about 25° C. and the water content in L-Ropivacaine hydrochloride by KF method was found to be 0.4%. The x-ray diffraction pattern of the material obtained is shown in FIG. 2.

EXAMPLE 13

Preparation of Hydrated L-Ropivacaine Hydrochloride 2 grams of dried L-Ropivacaine hydrochloride obtained through the process described in example 12 was exposed to humidity at about 75% RH at about temperature of 40° C. for about 20 hours in a controlled environment. The product obtained was found to be mixture of hydrated L-ropivacaine hydrochloride and L-ropivacaine hydrochloride monohydrate as indicated in the observed X-ray diffraction pattern shown in FIG. 3.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A process for the preparation of pure L-N-pipecolylxylidide, comprising:
    (a) preparing L-pipecolic acid chloride hydrochloride from pure L-pipecolic acid hydrochloride phosphorous pentachloride at a temperature range of about −30° C. to 20° C.; and
    (b) reacting the L-pipecolic acid chloride hydrochloride obtained in step (a) with xylidine at a temperature range of about −30° C. to 20° C. to produce optically pure L-N-pipecolylxylidide.

2. The process of claim 1, further comprising the step of making an anesthetic from the L-N-pipecolylxylidide obtained in step (b).

3. The process of claim 2, wherein the anesthetic is L N-pipecolylxylidide having the structure

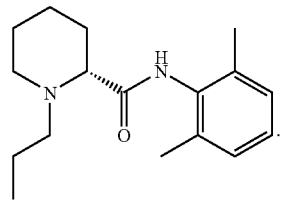

* * * * *